US010151718B2

(12) United States Patent
Tanaka et al.

(10) Patent No.: US 10,151,718 B2
(45) Date of Patent: Dec. 11, 2018

(54) QUANTITATIVE ANALYSIS DEVICE FOR TRACE CARBON AND QUANTITATIVE ANALYSIS METHOD FOR TRACE CARBON (71) Applicant: JFE STEEL CORPORATION, Tokyo (JP)

(72) Inventors: Yuji Tanaka, Tokyo (JP); Takako Yamashita, Tokyo (JP); Masayasu Nagoshi, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 54 days.

(21) Appl. No.: 15/528,330

(22) PCT Filed: Mar. 23, 2015

(86) PCT No.: PCT/JP2015/058690
§ 371 (c)(1),
(2) Date: May 19, 2017

(87) PCT Pub. No.: WO2016/084399
PCT Pub. Date: Jun. 2, 2016

(65) Prior Publication Data
US 2017/0336336 A1 Nov. 23, 2017

(30) Foreign Application Priority Data
Nov. 28, 2014 (JP) ................ 2014-242030

(51) Int. Cl.
*H01J 37/26* (2006.01)
*G01N 23/083* (2018.01)
(Continued)

(52) U.S. Cl.
CPC ....... *G01N 23/2252* (2013.01); *G01N 23/207* (2013.01); *H01J 37/18* (2013.01); *H01J 37/256* (2013.01); *H01J 37/28* (2013.01)

(58) Field of Classification Search
CPC ... G01N 23/2252; G01N 23/207; H01J 37/18; H01J 37/256; H01J 37/28
(Continued)

(56) References Cited

U.S. PATENT DOCUMENTS

| 6,436,615 B1 * | 8/2002 | Brandow ................. G03F 7/26 |
| | | 427/304 |
| 2006/0138363 A1 | 6/2006 | Yonezawa et al. |

(Continued)

FOREIGN PATENT DOCUMENTS

| EP | 2 757 572 A1 | 7/2014 |
| JP | H09-237602 A | 9/1997 |

(Continued)

OTHER PUBLICATIONS

Apr. 14, 2015 International Search Report issued in International Patent Application No. PCT/JP2015/058690.
(Continued)

*Primary Examiner* — Nicole Ippolito
(74) *Attorney, Agent, or Firm* — Oliff PLC (57) ABSTRACT

The present invention makes it possible to analyze trace carbon in a sample without the effects of contamination. In an electron probe microanalyzer, a liquid nitrogen trap and a plasma or oxygen radical generator are jointly used as a means for suppressing contamination, and two or more carbon detection units for detecting characteristic x-rays of carbon in the sample are provided.

17 Claims, 4 Drawing Sheets

(51) Int. Cl.
    *G01N 23/2252* (2018.01)
    *G01N 23/207* (2018.01)
    *H01J 37/28* (2006.01)
    *H01J 37/256* (2006.01)
    *H01J 37/18* (2006.01)

(58) Field of Classification Search
    USPC .......... 250/306, 307, 310, 311, 492.1, 492.2, 250/492.21, 492.22, 492.23, 492.3
    See application file for complete search history.

(56) References Cited

U.S. PATENT DOCUMENTS

| | | | | |
|---|---|---|---|---|
| 2006/0145067 | A1* | 7/2006 | Kalachev | G01N 21/71 250/282 |
| 2011/0139726 | A1* | 6/2011 | Jin | B01D 39/06 210/748.08 |
| 2011/0180385 | A1* | 7/2011 | Imholt | B01J 19/126 204/157.15 |
| 2012/0283342 | A1* | 11/2012 | Dalai | B01J 21/185 518/714 |

FOREIGN PATENT DOCUMENTS

| | | |
|---|---|---|
| JP | 2001-27621 A | 1/2001 |
| JP | 2001-283761 A | 10/2001 |
| JP | 2005-281750 A | 10/2005 |
| JP | 2006-164893 A | 6/2006 |
| JP | 2008-091270 A | 4/2008 |
| JP | 2010-160080 A | 7/2010 |
| JP | 4499125 B2 | 7/2010 |
| JP | 2011-34895 A | 2/2011 |
| JP | 2013-12454 A | 1/2013 |

OTHER PUBLICATIONS

Nov. 27, 2017 Extended Search Report issued in European Patent Application No. 15862942.8.
Mar. 5, 2018 Office Action issued in Chinese Patent Application No. 201580063795.3.
Jul. 20, 2018 Office Action issued in Korean Patent Application No. 10-2017-7013564.

\* cited by examiner

QUANTITATIVE ANALYSIS DEVICE FOR TRACE CARBON AND QUANTITATIVE ANALYSIS METHOD FOR TRACE CARBON

TECHNICAL FIELD

The present invention relates to a device for quantitative trace carbon analysis and a method for quantitative trace carbon analysis.

BACKGROUND ART

Steel is an alloy of iron and carbon, and materials with a variety of characteristics can be produced as desired by controlling the carbon content and a working and heat treatment method. Accordingly, quantitative analysis of carbon in steel materials is an extremely important technique for controlling material characteristics.

From this point of view, techniques for analyzing the carbon content of, for instance, a billet or molten steel have been developed, and quantitative analysis of not more than 0.1% carbon in terms of mass % is now possible. For example, Patent Literature 1 describes a method enabling the carbon concentration in molten steel to be estimated accurately with an error of up to 10 ppm. Those techniques are used for accurately analyzing the carbon content of a material for the average composition.

Meanwhile, even with the same carbon content, mechanical characteristics of steel materials can be greatly changed depending on the condition of the working and heat treatment method. Such mechanical characteristics are determined by metallographic structure of iron and steel materials. The distribution and existence form of carbon in a micrometer or smaller scale play important roles in control of metallographic structure. Thus, the analysis of trace carbon in metallographic structure is extremely important.

Optical microscopes and electron microscopes are often used in analysis of metallographic structure. In particular, when an electron microscope is used, a metallographic structure with a size of less than 1 μm can be observed. Furthermore, a device for detecting characteristic X-rays that are generated from samples upon irradiation with incident electron beams can be installed on an electron microscope. Use of such a device makes it possible to perform qualitative and quantitative analyses of elements, such as carbon, composing metallographic structure and being distributed with a size of less than 1 μm.

In recent years, the structure control of steel materials has been highly advanced, and use of dual phase steel having a plurality of metallographic structures in a steel material is not unusual. Therefore, it becomes increasingly important to analyze, in addition to the average chemical composition of a steel material, information on a local chemical composition corresponding to metallographic structure, particularly the distribution of carbon.

CITATION LIST

Patent Literature

Patent Literature 1: JP 2005-281750 A
Patent Literature 2: JP 4499125 B

SUMMARY OF INVENTION

Technical Problems

For quantifying carbon in steel materials with high accuracy in ppm level, a wet chemical analysis method disclosed in Patent Literature 1 is widely used, for example. However, a chemical analysis method is applicable to the examination of average composition and is not useful in measurement of local carbon concentration corresponding to metallographic structure.

Use of an analytical electron microscope in which a specific device is installed on an electron microscope makes it possible to analyze elements in a local region while observing metallographic structure. Examples of such a device include an energy dispersive X-ray spectrometer (EDS) using a semiconductor detector and a wavelength dispersive X-ray spectrometer (WDS) using an analyzing crystal and an X-ray detector. In particular, for analysis of light elements such as carbon, WDS having high sensitivity is typically used to perform point analysis or area analysis that is performed by scanning an electron beam.

Meanwhile, since the content of an element added to control a steel microstructure is often 0.01 to 1 mass % and thus extremely low, the influence of sample contamination to be described later has become a problem. In particular, carbon is the most important element that influences the characteristics of steel materials, and therefore, the influence of contamination is quite a serious problem.

The term "contamination" refers to a phenomenon in which residual gas components of organic substances slightly present in vacuum in a device are decomposed upon exposure to an electron beam, and carbon and hydrogen which are components composing the residual gas selectively adhere to an electron beam irradiated region of a sample; and also the term sometimes refers to an adhering substance itself.

Contaminations are quickly formed upon electron beam irradiation and cover a surface of a sample, which makes observation and analysis difficult. In addition, since contaminations are mainly composed of carbon, even when the analysis of carbon is carried out, it is impossible to determine whether analysis results are attributable to target carbon present in the sample or carbon present in contaminations.

To cope with it, in carbon analysis using an electron microscope, a liquid nitrogen trap is typically used which adsorbs residual gas in a sample chamber to reduce the amount of residual gas serving as a contamination source.

Such a liquid nitrogen trap is, however, not sufficiently effective. In area analysis of trace carbon, contamination increases with increasing analyzing time, and consequently, the analysis ends up with relatively high measurements of carbon distribution at the analysis end position, and that is a problem.

Patent Literature 2 discloses a method involving measuring an increase in carbon of contaminations with respect to an analysis measurement time in advance, and based thereon, making corrections during quantitative analysis. The amount of generated contaminations, however, varies with measurement conditions and from day to day, and accordingly, an increase in contaminations has to be measured in advance for every measurement. This is troublesome, and in addition, the accuracy may be insufficient.

The present invention has been made in view of the above and aims at providing a device for quantitative trace carbon analysis and a method for quantitative trace carbon analysis that are capable of analyzing trace carbon present in a sample without the influence of contamination.

Solution to Problems

The present inventors have made an intensive study to achieve the object and as a result found that when, as means for reducing contamination, a liquid nitrogen trap and a plasma or oxygen radical generator are used in combination and two or more carbon detecting sections for detecting characteristic X-rays of carbon are provided, trace carbon in a sample can be quantitatively determined without the influence of contamination.

Specifically, the present invention provides the following (1) to (9).

(1) A device for quantitative trace carbon analysis comprising:
  a sample chamber to be evacuated;
  a liquid nitrogen trap configured to trap residual gas in the sample chamber through cooling using liquid nitrogen;
  a plasma or oxygen radical generator configured to blow plasma or oxygen radicals onto a sample surface in the sample chamber and interior of the sample chamber;
  an electron source configured to generate an electron beam;
  a lens section configured to cause the generated electron beam to be focused;
  a scan driving section configured to cause the focused electron beam to be scanned on a sample in the sample chamber or drive a sample in the sample chamber with the focused electron beam being fixed; and
  carbon detecting sections each configured to detect a characteristic X-ray of carbon emitted from a sample irradiated with an electron beam,
  wherein the carbon detecting sections installed are two or more in number, and
  wherein trace carbon in a sample in the sample chamber is quantified from characteristic X-rays of carbon detected by the two or more carbon detecting sections.

(2) The device for quantitative trace carbon analysis according to (1), further comprising a sample heating section configured to heat and retain a sample in the sample chamber at a temperature of 50° C. or higher during electron beam irradiation.

(3) The device for quantitative trace carbon analysis according to (1) or (2), further comprising a sputtering section configured to sputter a sample surface in the sample chamber.

(4) The device for quantitative trace carbon analysis according to any one of (1) to (3), further comprising:
  a sample preparation chamber in which a sample is placed from an external environment and which is evacuated; and
  a second plasma or oxygen radical generator configured to blow plasma or oxygen radicals onto a sample surface in the sample preparation chamber.

(5) The device for quantitative trace carbon analysis according to any one of (1) to (4), wherein the carbon detecting sections are each a wavelength dispersive X-ray spectrometer having an analyzing crystal and an X-ray detector.

(6) A method for quantitative trace carbon analysis using the device for quantitative trace carbon analysis according to (1), the method comprising the steps of:
  trapping residual gas in the sample chamber by the liquid nitrogen trap;
  blowing plasma or oxygen radicals onto a sample surface in the sample chamber and the interior of the sample chamber by the plasma or oxygen radical generator prior to electron beam irradiation; and
  quantifying trace carbon in a sample in the sample chamber from characteristic X-rays of carbon as detected by the two or more carbon detecting sections.

(7) The method for quantitative trace carbon analysis according to (6), comprising the step of heating and retaining a sample in the sample chamber at a temperature of 50° C. or higher during electron beam irradiation.

(8) The method for quantitative trace carbon analysis according to (6) or (7), comprising the step of sputtering a sample surface in the sample chamber prior to electron beam irradiation.

(9) The method for quantitative trace carbon analysis according to any one of (6) to (8), wherein when area analysis is performed on a sample in the sample chamber, a region which spreads outward of an analysis target region of the sample is defined as an electron beam irradiation region to be irradiated with an electron beam, and the area analysis is performed only while the analysis target region is irradiated with an electron beam.

Advantageous Effects of Invention

The present invention can provide a device for quantitative trace carbon analysis and a method for quantitative trace carbon analysis that are capable of analyzing trace carbon present in a sample without the influence of contamination.

DESCRIPTION OF EMBODIMENTS

First, details about what led to the present invention will be explained.

A liquid nitrogen trap is widely known as means for reducing contamination in an electron microscope. The present inventors confirmed that a liquid nitrogen trap installed on an electron microscope is effective at reducing contamination. Liquid nitrogen cooling enabled qualitative analysis of the degree of carbon concentration of a sample. Even with such a liquid nitrogen trap, however, the adhesion of contaminations was unavoidable during analysis, so that the qualitative analysis was only possible.

Likewise, the present inventors confirmed that the qualitative analysis of carbon is possible by using a device blowing plasma or oxygen radicals onto a sample and the interior of a sample chamber of an electron microscope. However, again, the adhesion of contaminations was unavoidable.

Next, the present inventors attempted to reduce contamination by using a liquid nitrogen trap and a plasma or oxygen radical generator (hereinafter also simply called "plasma generator") in combination. Contamination was further reduced owing to the combination use but still adhered, and thus the carbon analysis without the influence of contamination was difficult.

In the meantime, the present inventors examined the intensity of a characteristic X-ray relative to an analysis time and found that contaminations are deposited more with increasing analysis time and the intensity of a characteristic X-ray of carbon increases with time. In other words, if an analysis is finished in a short time, the influence of contamination can substantially be ignored in carbon analysis.

Signals for analysis are, however, not sufficiently obtained in a brief analysis, and therefore, particularly in the analysis of trace component, the detection itself is to be difficult. To increase the amount of characteristic X-ray signals, increasing probe current is effective. With this, however, the amount of signals from the main component of the matrix is also increased.

EDS widely used for element analysis along with an electron microscope can simultaneously detect signals of all elements, but the amount of signals that EDS can detect and process per unit time is limited. Therefore, the amount of probe current can be increased to only a limited degree for the purpose of analyzing trace components because the amount of signals from the matrix becomes excessive in EDS.

To cope with it, the present inventors focused attention on WDS, which is another means for detecting characteristic X-rays. Although unable to simultaneously detect multiple elements, WDS can analyze a single target element to the exclusion of excessive signals from the matrix, and accordingly, the amount of current can be increased in trace component analysis.

The present inventors used an electron probe micro analyzer (EPMA) having WDS thereon with the use of a liquid nitrogen trap and a plasma generator in combination. As a result, it was revealed that, if what is employed is point analysis or line analysis, a local carbon concentration of an unknown sample can be quantified accurately with an error of up to 1 mass % through a calibration curve method using samples with known carbon concentration.

In an area analysis in which an analysis time for each point was short, however, the amount of signals was insufficient for quantitative analysis, while the degree of carbon concentration was able to be qualitatively determined. A longer analysis time leads to heavier contamination, which prevents the analysis from being accurately performed, and therefore, the inventors thought about improving the sensitivity of an X-ray detector.

Since WDS installed on EPMA can measure only one element at a time, from the standpoint of convenience, a plurality of WDS are typically installed on EPMA. Besides, EPMA is expected to be used for analysis of a variety of samples and elements, and therefore, analyzing crystals for WDS are combined so as to be useful in measurement of from light to heavy elements in a single analysis process. Further, for WDS installed on EPMA, analyzing crystals of types that are as different as possible are generally combined because it is necessary to separately use an analyzing crystal having high wavelength resolution and an analyzing crystal allowing many X-ray intensities to be measured, depending on the analysis purpose.

Thus, conventionally, analyzing crystals to be installed in EPMA have been combined in a versatile manner in order to deal with a variety of samples and analysis purposes.

In the circumstances, the present inventors did a test involving replacing, among analyzing crystals for a plurality of WDS installed on EPMA, at least two by other analyzing crystals that allow characteristic X-rays of carbon to be detected. It was revealed that this replacement drastically improves the sensitivity of carbon analysis and accordingly, the intensity of characteristic X-rays can be quantitatively discussed even through area analysis in which an analysis time for each point is short.

In the analysis of complex metallographic structure, it is extremely important to know an element concentration distribution of the whole sample through area analysis rather than point or line analysis. However, means for quantitative analysis of carbon through area analysis has been unknown to date.

The present inventors found that quantitative area analysis of carbon is possible by employing the configuration in which EPMA is provided with at least two analyzing crystals allowing characteristic X-rays of carbon to be detected and at least two X-ray detectors. The present inventors further found that use of a liquid nitrogen trap and a plasma generator in combination leads to a reliable quantitative value unaffected by contamination. The technique enabling quantitative analysis of trace carbon to be done through area analysis is a totally new function that conventional EPMA does not have. In addition, the technique enabling quantitative analysis of trace carbon to be done through area analysis is an extremely important and epoch-making technique in development of materials such as steels.

Next, one embodiment of a device for quantitative trace carbon analysis (hereinafter also simply called "device") of the invention is described based on FIGS. 1 and 2.

Figure 1:
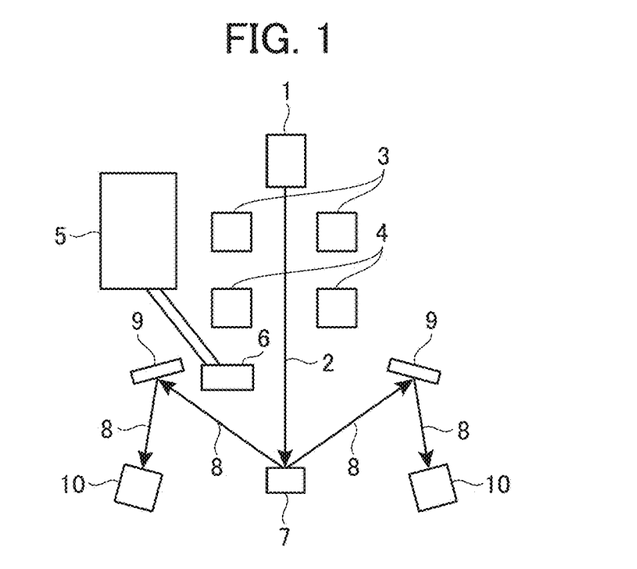
FIG. 1 is a schematic configuration view showing a part of a device for quantitative trace carbon analysis.
Figure 2:
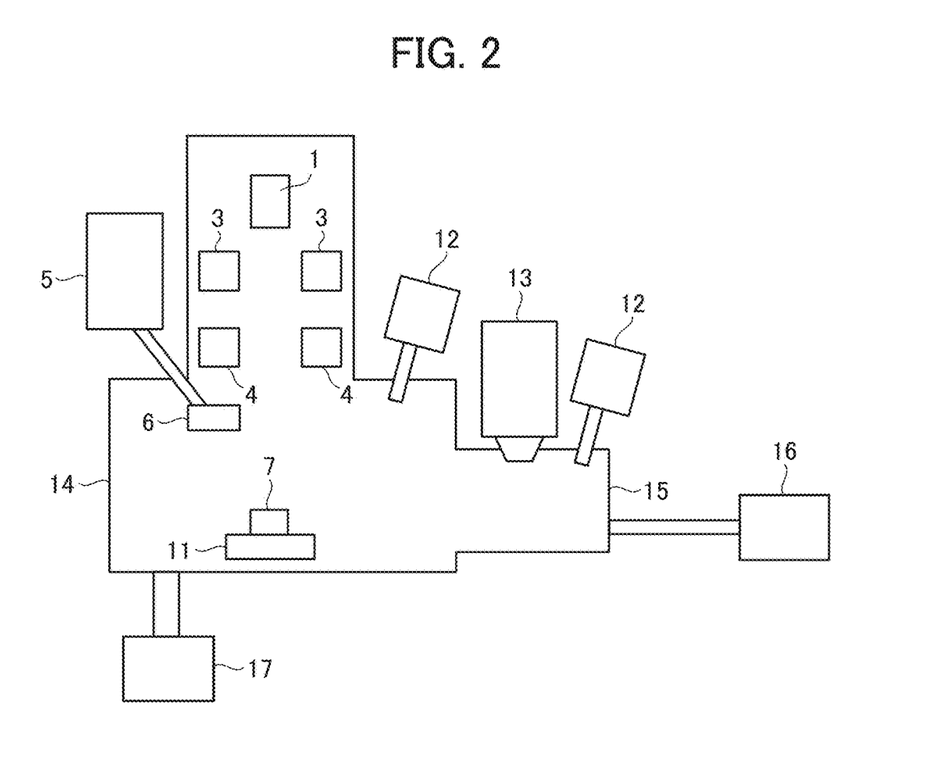
FIG. 2 is a schematic configuration view showing the device for quantitative trace carbon analysis.

FIG. 1 is a schematic configuration view showing a part of a device for quantitative trace carbon analysis. FIG. 2 is a schematic configuration view showing the device for quantitative trace carbon analysis.

An electron beam 2 generated by an electron source 1 is focused through a condenser lens 3 and an objective lens 4 which constitute a lens section. The focused electron beam 2 is controlled by a scanning coil a (see FIG. 7), serving as a scan driving section, to scan across a sample 7 placed on a sample stage 11. Alternatively, the sample 7 is driven by the sample stage 11, serving as a scan driving section, with the focused electron beam 2 being fixed. Thus the sample 7 is irradiated with the electron beam 2. Characteristic X-rays 8 generated (or emitted) from the sample 7 upon irradiation with the electron beam 2 are directed to X-ray detectors 10 by means of analyzing crystals 9, and the intensities of characteristic X-rays emitted from the sample 7 are recorded. For the device configuration, see also FIG. 7.

At least two analyzing crystals 9 and at least two X-ray detectors 10 are incorporated in the device. Among a plurality of incorporated analyzing crystals 9, at least two are elements that can disperse characteristic X-rays of carbon. One example of such an element is an artificial multilayer film, namely, a layered dispersion element (LDE).

There are provided at least two, preferably at least three carbon detecting sections each of which is made up of an analyzing crystal 9 and an X-ray detector 10 and is configured to detect characteristic X-rays of carbon, the analyzing crystal 9 being an element that allows dispersion of characteristic X-rays of carbon. The upper limit of the number of the carbon detecting sections is not particularly specified and appropriately set according to spatial constraints of a sample chamber 14.

When only carbon analysis is carried out, the configuration may be employed in which all the analyzing crystals 9 and X-ray detectors 10 allow dispersion of characteristic X-rays of carbon. When it is necessary to analyze other elements than carbon, the configuration may be employed in which some of analyzing crystals 9 allow analysis of such elements.

A liquid nitrogen trap 6 is cooled by liquid nitrogen filled in a liquid nitrogen tank 5 and adsorbs residual gas in the sample chamber 14, thereby reducing the generation of contamination.

The sample 7 is driven by the sample stage 11 in the sample chamber 14, as described above. For the sample stage 11, a heating stage to be described later may be used.

A plasma or oxygen radical generator 12 is disposed at the sample chamber 14 and operated before or after the sample 7 is irradiated with the electron beam 2. Since plasma or oxygen radical serves to not only clean a surface of the sample 7 but also reduce contamination generated from the sample chamber 14, the plasma or oxygen radical generator 12 is preferably disposed at the sample chamber 14.

Another plasma or oxygen radical generator 12 (second plasma or oxygen radical generator) may be disposed at a sample preparation chamber 15 positioned adjacent to the sample chamber 14 via an openable partition (not shown).

In this case, firstly, the sample 7 is brought from the external environment and set in the sample preparation chamber 15 with the partition being closed. As the sample preparation chamber 15 is evacuated by a vacuum pump 16, plasma or oxygen radical is blown onto the surface of the sample 7 in the sample preparation chamber 15 by the plasma or oxygen radical generator 12 disposed at the sample preparation chamber 15. Subsequently, the partition is opened and the sample 7 is transferred to the sample chamber 14, and plasma or oxygen radical is blown onto the surface of the sample 7 in the sample chamber 14 and the interior of the sample chamber 14 by the plasma or oxygen radical generator 12 disposed at the sample chamber 14.

When use is made of the device of draw-out type with no sample preparation chamber 15, in which device the sample 7 is directly set in the sample chamber 14, the plasma or oxygen radical generator 12 is disposed only at the sample chamber 14.

Contaminations thickly deposited on the surface of the sample 7 through pre-adjustment of the sample 7 and irradiation with the electron beam 2 are sometimes not easily removable by the plasma or oxygen radical generator 12. In order to remove such contaminations in the device, an ion gun 13 may be installed as a sputtering section for sputtering the surface of the sample 7. The ion gun 13 is preferably disposed not at the sample chamber 14 but at the sample preparation chamber 15 because the surroundings may be contaminated due to ion sputtering such as argon sputtering. Ion sputtering serves to remove contaminations on the surface of the sample 7 so as to allow the clean surface of the sample 7 to be exposed, thus leading to accurate carbon analysis. In addition, ion sputtering serves to remove a polishing strain phase from the surface of the sample 7 and, if the sample is a metal material, allow fine irregularities corresponding to the microfine structure to be formed at the sample surface. Owing to this, an object of interest to be measured can easily be found using a microscope function of the device.

The sample chamber 14 and the sample preparation chamber 15 are evacuated by a vacuum pump 17 and the vacuum pump 16, respectively.

Meanwhile, contamination sources in the device include, in addition to substances adhering to the sample, substances occurring from the device itself. For instance, a contamination source may be brought in from a vacuum pump which is an essential component of the device. Such a contamination source derives from oil in the vacuum pump, and accordingly, it is preferable to employ a vacuum pump that does not use oil. From such a rotary pump that is often used for roughly evacuating a sample preparation chamber released to atmosphere, oil components therein sometimes flow back.

To deal with it, for example, dry pumps are preferably used as the vacuum pump 16 of the sample preparation chamber 15 and a vacuum pump (not shown) for rough pumping of the sample chamber 14. As the vacuum pump 17 of the sample chamber 14 provided for achieving a higher degree of vacuum, for instance, a turbomolecular pump is preferably used while an oil diffusion pump is not preferred.

Figure 3:
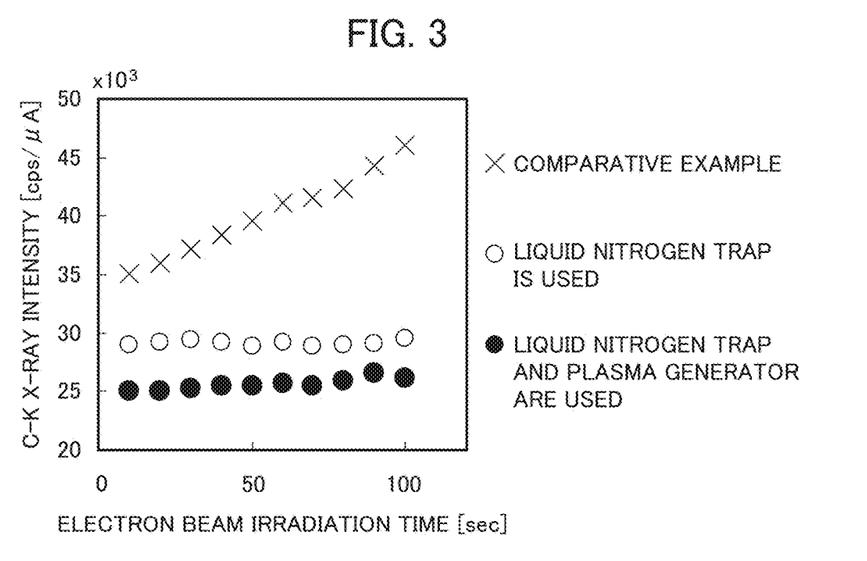
FIG. 3 is a graph showing the relationships between electron beam irradiation times and C-K characteristic X-ray intensities when a liquid nitrogen trap and a plasma generator were used in combination and when they were not used in combination.

Next, the technical significance of use of a liquid nitrogen trap and a plasma or oxygen radical generator in combination is described based on FIG. 3.

The present inventors compared the adhesion of contaminations when a liquid nitrogen trap and a plasma generator were used in combination to the adhesion of contaminations when they were not used in combination. To be more specific, the C-K characteristic X-ray intensity occurring when an iron-carbon reference sample (C amount: 0.089 mass %; balance: iron) for EPMA was irradiated with an electron beam was measured using EPMA (JXA-8530F) manufactured by JEOL Ltd. The relationship between an accumulated electron beam irradiation time and a measured X-ray intensity when the same portion of the sample was irradiated with an electron beam was examined.

FIG. 3 is a graph showing the relationships between electron beam irradiation times and C-K characteristic X-ray intensities when a liquid nitrogen trap and a plasma generator were used in combination and when they were not used in combination.

As can be seen in the graph of FIG. 3, in the comparative example (in which neither a liquid nitrogen trap nor a plasma generator was used), the C-K characteristic X-ray intensity increases with increasing electron beam irradiation time, and this leads to the fact that contaminations mainly composed of C were gradually deposited on a sample surface.

In contrast, it can be seen that when only a liquid nitrogen trap is used (with no plasma generator), the X-ray intensity remains substantially constant with respect to the irradiation time, which leads to the fact that contaminations were prevented from being newly deposited.

Next, a plasma generator (GV10x DS) manufactured by ibss Group Inc. was attached at a sample chamber of the EPMA, and plasma was generated for five minutes to clean the sample surface and the sample chamber. Subsequently, the same measurement was carried out using the liquid nitrogen trap. Then it was found that the C-K characteristic X-ray intensity further decreases compared to that obtained when only the liquid nitrogen trap is used. This revealed that contaminations on the sample surface are removed by the plasma generator so that the X-ray intensity according to the C content of the sample itself can be measured. Further, the X-ray intensity is different from that obtained when only the liquid nitrogen trap is used, and therefore, it is understood that contaminations originally adhering to the surface are also subjected to measurement when only the liquid nitrogen trap is used. Since the amount of adhering contaminations varies depending on the timing of sample preparation, carbon analysis cannot repeatedly be carried out in a reproducible manner only with a liquid nitrogen trap. Thus, it is not until contaminations are prevented from being newly deposited using a liquid nitrogen trap and contaminations adhering to a sample surface are removed using a plasma generator that carbon originally contained in a sample can be accurately measured.

Meanwhile, it can be seen from the graph of FIG. 3 that even when the liquid nitrogen trap and the plasma generator are used in combination, the X-ray intensity increases with increasing electron beam irradiation time after the elapse of electron beam irradiation time of 50 seconds, albeit only slightly. Shown in FIG. 3 are the results of analyses carried out for the same portion of the sample, and therefore it is possible to again do analyses without the influence of contamination if the portion to be analyzed is changed to a region having not been irradiated with an electron beam.

In line analysis and area analysis using EPMA, however, the analysis is carried out while an electron beam is continuously scanned or a sample is continuously driven, and accordingly, the influence of contaminations at the portion having been analyzed immediately before is accumulated. Even when a liquid nitrogen trap and a plasma generator are used in combination, in area analysis (mapping analysis) that requires an analysis time of more than 30 minutes, the C-K characteristic X-ray intensity increases immediately before the analysis finishes, and thus the carbon distribution cannot accurately be measured due to contamination. In point analysis and line analysis, the measurement can be finished before being affected by contamination owing to the use of a liquid nitrogen trap and a plasma generator in combination; however, in area analysis that requires a long measurement time, it is difficult for conventional EPMA to secure the sufficient amount of signals with reduced contamination in measurement.

Figure 4:
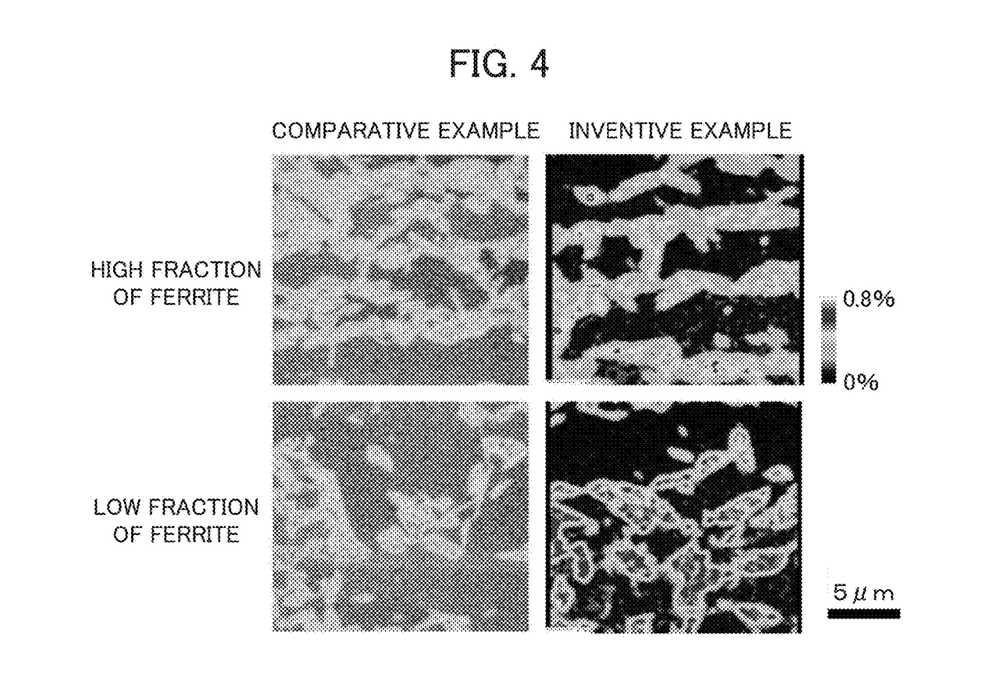
FIG. 4 shows results of area analysis on carbon present in steel.

Next, the technical significance of provision of two or more carbon detecting sections for detecting characteristic X-rays of carbon is described based on FIG. 4.

As described above, when area analysis is performed with an electron beam scanned or a sample driven, the use of a liquid nitrogen trap and a plasma or oxygen radical generator in combination allows the analysis to be done with reduced influence of contamination for 30 minutes after the start of electron beam irradiation. Assuming that the analysis time is 30 minutes, when the area analysis is performed for, for instance, 256×256 pixels, the analysis time is to be about 25 milliseconds for each pixel. The quantitative precision in terms of carbon with this analysis time is estimated to be about 0.5 mass % (3σ) based on the statistical dispersion of the amount of X-ray. This level of precision is so insufficient in steel analysis that only a qualitative difference according to the amount of carbon is allowed to be discussed.

However, the sensitivity can be improved by increasing the number of carbon detecting sections (analyzing crystals and X-ray detectors) for detecting characteristic X-rays of carbon. For example, when the amount of C-K characteristic X-rays was measured by simultaneously using three carbon detecting sections (analyzing crystals and X-ray detectors), the analysis precision was improved to 0.3 mass %. This difference in quantitative analysis precision is extremely important in steel area analysis.

FIG. 4 shows results of area analysis on carbon present in steel. A sample is ferrite-martensite dual phase steel with the composition of Fe-0.13C-1.4Si-2Mn (where the numbers are given in percent by mass). In each of Comparative Example and Inventive Example, two types of steels with different fractions of ferrite were analyzed, with the fraction of ferrite being varied by changing the heat treatment temperature. The amount of carbon in a ferrite phase is known to be not more than 0.02 mass %, and much of additive carbon is distributed in a martensite phase which is a phase other than the ferrite phase and is the second phase. Accordingly, even with the same amount of additive carbon, the carbon concentration in the martensite phase varies due to the difference in fraction of ferrite.

In FIG. 4, the carbon concentration is expressed by the density of shading (contrast). For instance, the ferrite phase corresponds to dark color regions while the martensite phase corresponds to light color regions.

In Comparative Example in FIG. 4, a liquid nitrogen trap and a plasma generator were used in combination, more specifically, EPMA (JXA-8530F) manufactured by JEOL Ltd. was used with only one carbon detecting section (an analyzing crystal and an X-ray detector) for detecting C-K characteristic X-rays to carry out area analysis for carbon. The analyzing crystal was an artificial multilayer film LDE6H. The area analysis was performed on pixels of 256×256 for 20 milliseconds per pixel. As shown in FIG. 4, in Comparative Example, the difference in carbon concentration between the ferrite phase and the martensite phase can be observed; however, due to less signals, the density of shading (contrast) in the martensite phase does not distinctively vary, and it is impossible to distinguish the difference in carbon concentration in the martensite phase between the two types of steels with different fractions of ferrite.

In the meantime, Inventive Example shown in FIG. 4 is an analysis example in which C-K characteristic X-rays were simultaneously detected by three carbon detecting sections. The analyzing crystals were artificial multilayer films LDE6H. Not only does the difference in carbon concentration between the ferrite phase and the martensite phase appear, but the density of shading (contrast) in the martensite phase also distinctively vary, and it is possible to distinguish the difference in carbon concentration in the martensite phase between the two types of steels with different fractions of ferrite.

According to the present invention, contamination is greatly reduced owing to the use of a liquid nitrogen trap and a plasma or oxygen radical generator in combination, and the sensitivity to trace carbon is improved owing to simultaneous use of two or more carbon detecting sections, thereby remarkably improving the reliability of values of quantitative analysis on carbon.

Therefore, the present invention is superior to conventional art not only in area analysis as described with reference to FIG. 4 but also in point analysis and line analysis.

Figure 5:
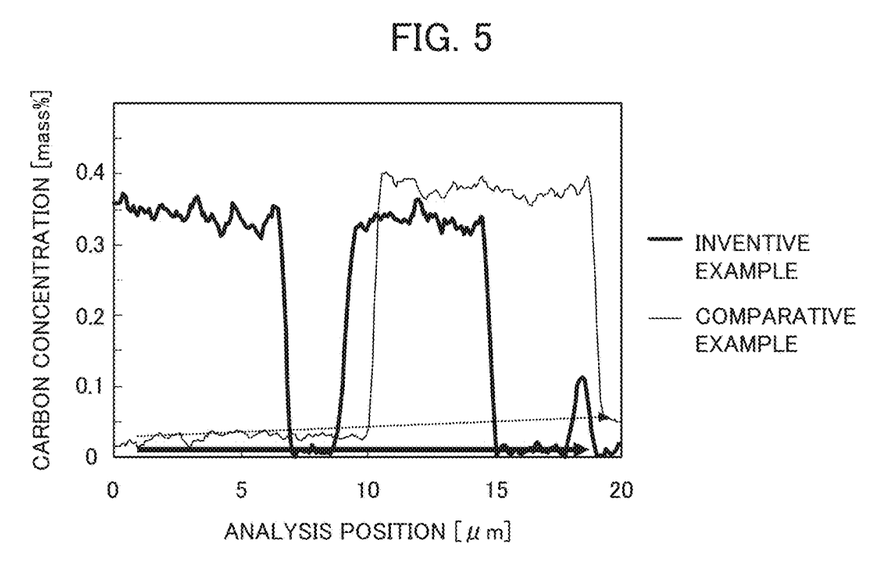
FIG. 5 shows results of line analysis on carbon present in steel.

FIG. 5 shows results of line analysis on carbon present in steel. A sample is ferrite-martensite dual phase steel with the composition of Fe-0.15C-2.0Si-1.5Mn (where the numbers are given in percent by mass).

In Comparative Example shown in FIG. 5, the line analysis was performed with only one carbon detecting section while seeking reduction in contamination by means of a liquid nitrogen trap. The results show that the quantitative value of carbon in the ferrite phase (indicated by dotted arrow in FIG. 5) increases with increasing value of analysis position. This is a result not reflecting the change in actual concentration but having been affected by contaminations deposited during the analysis and thus, the contaminations caused the quantitative value to increase. Hence, the quantitative value with a carbon concentration of up to 0.05 mass % is not reliable.

On the other hand, in Inventive Example shown in FIG. 5, the line analysis was performed with the use of a liquid nitrogen trap and a plasma generator in combination as well as three carbon detecting sections. As a result, even when the value of analysis position increased, the increase in the quantitative value of carbon (indicated by thick arrow in FIG. 5) was not seen, and thus carbon originally present in the sample was able to be quantitatively determined without the influence of contamination.

The quantitative value of carbon in the martensite phase having a higher carbon concentration than that of the ferrite phase is also different between Inventive Example and Comparative Example in FIG. 5. The carbon concentration of the martensite phase of the sample was 0.32 mass % as a result of theoretical calculation by diffusion control type transformation calculation software. The carbon concentration of the martensite phase was 0.33 mass % in average in Inventive Example shown in FIG. 5 and 0.38 mass % in Comparative Example shown in FIG. 5. In other words, Inventive Example allowed the carbon concentration to be analyzed with an error of 0.01 mass % with respect to a predictive value theoretically obtained, while in Comparative Example, the analysis error due to contamination was not less than 0.05 mass %, and the quantitative value inevitably varied between the start and end points of analysis due to contamination.

Figure 6:
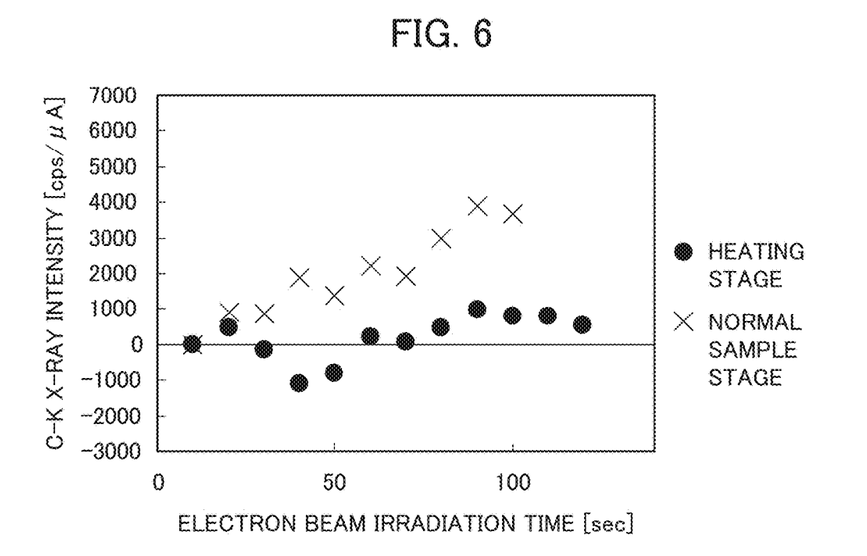
FIG. 6 is a graph showing the relationships between electron beam irradiation times and C-K characteristic X-ray intensities when a normal sample stage was used and when a heating stage was used.

Next, the case where a heating stage (sample heating section) is used as the sample stage (designated by reference numeral 11 in FIG. 2) of the device is described based on FIG. 6. A heating stage capable of heating and retaining a sample at a temperature of 50° C. or higher serves to prolong the time taken until contaminations are deposited on a sample surface after the start of electron beam irradiation, thereby further reducing the influence of contamination.

The present inventors examined the relationship between the electron beam irradiation time and the C-K characteristic X-ray intensity when point analysis was performed by heating and holding the sample at 110° C. with a positive temperature coefficient (PTC) thermistor. To be more specific, taking the X-ray intensity with an electron beam irradiation time of 10 seconds as the reference, the difference from the reference intensity was examined with respect to the electron beam irradiation time. EPMA (JXA-8530F) manufactured by JEOL Ltd. was used with three carbon detecting sections for detecting characteristic X-rays of carbon. A liquid nitrogen trap and a plasma generator were used in combination, and a sample surface was sputtered with argon by an ion gun disposed at a sample preparation chamber before the analysis was started by irradiating the sample with an electron beam. The results are shown in FIG. 6.

FIG. 6 is a graph showing the relationships between electron beam irradiation times and C-K characteristic X-ray intensities when a normal sample stage was used and when a heating stage was used.

It can be seen from the graph of FIG. 6 that with the use of a normal sample stage, the X-ray intensity significantly increases when the electron beam irradiation time exceeds 50 seconds, and thus the influence of contamination is seen even with the use of a liquid nitrogen trap and a plasma generator in combination. In contrast, it was revealed that with a sample being heated and retained at a certain temperature by a heating stage, the X-ray intensity does not increase even when the electron beam irradiation time exceeds 100 seconds, and thus the influence of contamination can be reduced.

Thus, the time to take until contaminations adhere to a sample can be prolonged also in area analysis and therefore, the analysis with higher quantitative precision can be carried out.

When the heating temperature is lower than 50° C., the adhesion of contaminations is not very effectively prevented. On the other hand, when the heating temperature is too high, properties of a sample may change, and sample drift due to heat cannot be easily prevented from occurring, so that the heating temperature is preferably not higher than 150° C.

Further, the present inventors conducted a study on contaminations adhering to a sample surface. As a result, it was revealed that contaminations are not evenly deposited over an electron beam irradiation region of the sample surface but deposited particularly on the edge of the electron beam irradiation region in a concentrated manner. In other words, even when contaminations are deposited on the edge of the electron beam irradiation region and this hampers accurate quantitative determination of carbon, the quantitative analysis on carbon is possible in the center part of the electron beam irradiation region. Accordingly, when area analysis is performed on a sample, a region which spreads outward of an interest region of the analysis (analysis target region) is defined as a region to be irradiated with an electron beam (electron beam irradiation region), and the area analysis is performed only while the analysis target region is irradiated with an electron beam. This allows the analysis to be performed without including the edge of the electron beam irradiation region and thus with reduced influence of contamination.

Figure 7:
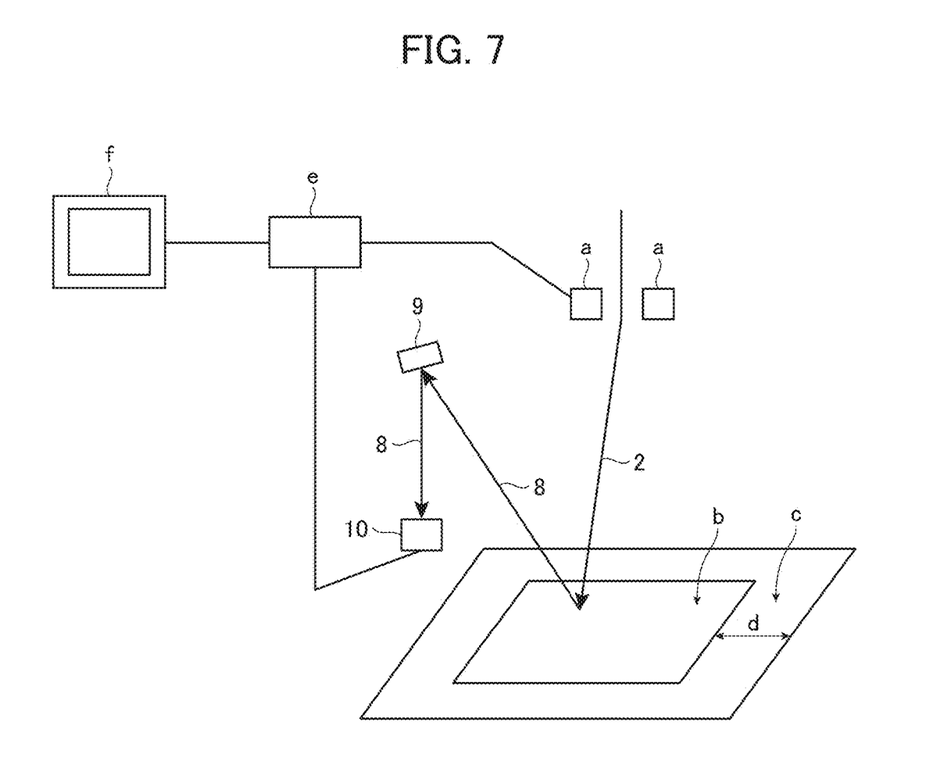
FIG. 7 is a schematic view showing one example of an area analysis method.

FIG. 7 is a schematic view showing one example of an area analysis method. The electron beam 2 scans the inside of an electron beam irradiation region c of the sample by the aid of the scanning coil a. Position information on the electron beam 2 deflected by the scanning coil a and X-ray intensity signals are input to a controller e. The controller e outputs X-ray intensity signals to an image output device f only while the electronic beam 2 is scanning an analysis target region b. The quantitative analysis can be carried out based on the X-ray intensity signals, comparing those signals with a reference sample data intensity.

When the analysis target region b and the electron beam irradiation region c both have a quadrangle shape and one side of the analysis target region b has a length of not more than 10 μm, the distance d between the outer frame of the analysis target region b and the outer frame of the electron beam irradiation region c is preferably not less than 1 μm but not more than 10 μm, and more preferably not less than 2 μm but not more than 7 μm. When one side of the analysis target region b has a length of more than 10 μm, the distance d is preferably 0.1 to 1.0 times, more preferably 0.2 to 0.7 times as long as the length of the one side of the analysis target region b.

REFERENCE SIGNS LIST

1: electron source
2: electron beam
3: condenser lens (lens section)
4: objective lens (lens section)
5: liquid nitrogen tank
6: liquid nitrogen trap
7: sample
8: characteristic X-ray
9: analyzing crystal (carbon detecting section)
10: X-ray detector (carbon detecting section)
11: sample stage (scan driving section, sample heating section)
12: plasma or oxygen radical generator
13: ion gun (sputtering section)
14: sample chamber
15: sample preparation chamber 16: vacuum pump
17: vacuum pump
a: scanning coil (scan driving section)
b: analysis target region
c: electron beam irradiation region
d: distance
e: controller
f: image output device

The invention claimed is:

1. A device for quantitative trace carbon analysis comprising:
   a sample chamber to be evacuated;
   a liquid nitrogen trap configured to trap residual gas in the sample chamber through cooling using liquid nitrogen;
   a plasma or oxygen radical generator configured to blow plasma or oxygen radicals onto a sample surface in the sample chamber and interior of the sample chamber;
   an electron source configured to generate an electron beam;
   a lens section configured to cause the generated electron beam to be focused;
   a scan driving section configured to cause the focused electron beam to be scanned on a sample in the sample chamber or drive a sample in the sample chamber with the focused electron beam being fixed; and
   carbon detecting sections each configured to detect a characteristic X-ray of carbon emitted from a sample irradiated with an electron beam,
   wherein the carbon detecting sections installed are two or more in number, and
   wherein trace carbon in a sample in the sample chamber is quantified from characteristic X-rays of carbon detected by the two or more carbon detecting sections.

2. The device for quantitative trace carbon analysis according to claim 1, further comprising a sample heating section configured to heat and retain a sample in the sample chamber at a temperature of 50° C. or higher during electron beam irradiation.

3. The device for quantitative trace carbon analysis according to claim 2, further comprising a sputtering section configured to sputter a sample surface in the sample chamber.

4. The device for quantitative trace carbon analysis according to claim 3, further comprising:
   a sample preparation chamber in which a sample is placed from an external environment and which is evacuated; and
   a second plasma or oxygen radical generator configured to blow plasma or oxygen radicals onto a sample surface in the sample preparation chamber.

5. The device for quantitative trace carbon analysis according to claim 2, further comprising:
   a sample preparation chamber in which a sample is placed from an external environment and which is evacuated; and
   a second plasma or oxygen radical generator configured to blow plasma or oxygen radicals onto a sample surface in the sample preparation chamber.

6. The device for quantitative trace carbon analysis according to claim 1, further comprising a sputtering section configured to sputter a sample surface in the sample chamber.

7. The device for quantitative trace carbon analysis according to claim 6, further comprising:
   a sample preparation chamber in which a sample is placed from an external environment and which is evacuated; and
   a second plasma or oxygen radical generator configured to blow plasma or oxygen radicals onto a sample surface in the sample preparation chamber.

8. The device for quantitative trace carbon analysis according to claim 1, further comprising:
   a sample preparation chamber in which a sample is placed from an external environment and which is evacuated; and
   a second plasma or oxygen radical generator configured to blow plasma or oxygen radicals onto a sample surface in the sample preparation chamber.

9. The device for quantitative trace carbon analysis according to claim 1, wherein the carbon detecting sections are each a wavelength dispersive X-ray spectrometer having an analyzing crystal and an X-ray detector.

10. A method for quantitative trace carbon analysis using the device for quantitative trace carbon analysis according to claim 1, the method comprising the steps of:
    trapping residual gas in the sample chamber by the liquid nitrogen trap;
    blowing plasma or oxygen radicals onto a sample surface in the sample chamber and the interior of the sample chamber by the plasma or oxygen radical generator prior to electron beam irradiation; and
    quantifying trace carbon in a sample in the sample chamber from characteristic X-rays of carbon as detected by the two or more carbon detecting sections.

11. The method for quantitative trace carbon analysis according to claim 10, comprising the step of heating and retaining a sample in the sample chamber at a temperature of 50° C. or higher during electron beam irradiation.

12. The method for quantitative trace carbon analysis according to claim 11, comprising the step of sputtering a sample surface in the sample chamber prior to electron beam irradiation.

13. The method for quantitative trace carbon analysis according to claim 12, wherein when area analysis is performed on a sample in the sample chamber, a region which spreads outward of an analysis target region of the sample is defined as an electron beam irradiation region to be irradiated with an electron beam, and the area analysis is performed only while the analysis target region is irradiated with an electron beam.

14. The method for quantitative trace carbon analysis according to claim 11, wherein when area analysis is performed on a sample in the sample chamber, a region which spreads outward of an analysis target region of the sample is defined as an electron beam irradiation region to be irradiated with an electron beam, and the area analysis is performed only while the analysis target region is irradiated with an electron beam.

15. The method for quantitative trace carbon analysis according to claim 10, comprising the step of sputtering a sample surface in the sample chamber prior to electron beam irradiation.

16. The method for quantitative trace carbon analysis according to claim 15, wherein when area analysis is performed on a sample in the sample chamber, a region which spreads outward of an analysis target region of the sample is defined as an electron beam irradiation region to be irradiated with an electron beam, and the area analysis is performed only while the analysis target region is irradiated with an electron beam.

17. The method for quantitative trace carbon analysis according to claim 10, wherein when area analysis is performed on a sample in the sample chamber, a region which spreads outward of an analysis target region of the sample is defined as an electron beam irradiation region to be irradiated with an electron beam, and the area analysis is performed only while the analysis target region is irradiated with an electron beam.

* * * * *